(12) United States Patent
Akita et al.

(10) Patent No.: US 9,212,988 B2
(45) Date of Patent: Dec. 15, 2015

(54) LIQUID CONCENTRATION DETECTOR FOR A BLOOD PURIFICATION APPARATUS

(75) Inventors: Kunihiko Akita, Shizuoka (JP); Tomoya Murakami, Shizuoka (JP); Takayuki Hirano, Shizuoka (JP); Yasushi Takakuwa, Shizuoka (JP)

(73) Assignee: NIKKISO CO., LTD., Tokyo (JP)

( * ) Notice: Subject to any disclaimer, the term of this patent is extended or adjusted under 35 U.S.C. 154(b) by 464 days.

(21) Appl. No.: 12/967,643

(22) Filed: Dec. 14, 2010

(65) Prior Publication Data

US 2011/0144459 A1 Jun. 16, 2011

(30) Foreign Application Priority Data

Dec. 14, 2009 (JP) .................... 2009-282878

(51) Int. Cl.
| | |
|---|---|
| B01D 11/00 | (2006.01) |
| B01D 61/00 | (2006.01) |
| C02F 1/44 | (2006.01) |
| G01N 21/27 | (2006.01) |
| A61M 1/16 | (2006.01) |
| G01N 21/59 | (2006.01) |
| G01N 21/05 | (2006.01) |

(52) U.S. Cl.
CPC ............... *G01N 21/274* (2013.01); *A61M 1/16* (2013.01); *A61M 1/1609* (2014.02); *G01N 21/59* (2013.01); *A61M 2205/3313* (2013.01); *G01N 21/05* (2013.01); *G01N 2201/0621* (2013.01); *G01N 2201/0626* (2013.01)

(58) Field of Classification Search
USPC .................. 210/88, 96.1, 647; 600/310
See application file for complete search history.

(56) References Cited

U.S. PATENT DOCUMENTS

| | | | | |
|---|---|---|---|---|
| 5,247,434 A | * | 9/1993 | Peterson et al. ................. | 700/83 |
| 6,666,840 B1 | | 12/2003 | Falkvall et al. | |
| 2002/0145122 A1 | | 10/2002 | Duchon et al. | |
| 2004/0067594 A1 | * | 4/2004 | Mori et al. ...................... | 436/70 |
| 2006/0012774 A1 | * | 1/2006 | O'Mahony et al. ............. | 356/39 |
| 2009/0054822 A1 | | 2/2009 | Murakami et al. | |

FOREIGN PATENT DOCUMENTS

| | | |
|---|---|---|
| CN | 2253204 Y | 4/1997 |
| JP | 61-155735 A | 7/1986 |
| JP | 02-223848 A | 9/1990 |
| JP | 11-226119 | 8/1999 |
| WO | 94/11093 A1 | 5/1994 |

* cited by examiner

*Primary Examiner* — Dirk Bass
(74) *Attorney, Agent, or Firm* — McDermott Will & Emery LLP

(57) ABSTRACT

A blood purification apparatus includes a blood purification instrument for extracorporeally circulating blood of a patient and a concentration detector detecting a concentration of liquid flowing during blood purification. The concentration detector has a light emitter irradiating light onto said liquid, a light receiver receiving light from the light emitter transmitted through said liquid, and a detector detecting the received light intensity received by the light receiver. The concentration detector detects the concentration of the liquid based on the received light intensity and can be calibrated by adjusting an amount of irradiation by the light emitter so that the received light intensity has a predetermined value.

6 Claims, 5 Drawing Sheets

LIQUID CONCENTRATION DETECTOR FOR A BLOOD PURIFICATION APPARATUS

CROSS REFERENCE TO RELATED APPLICATIONS

The present application claims priority under 35 U.S.C. §119 to Japanese Patent Application No. 2009-282878, filed Dec. 14, 2009, which is incorporated herein by reference.

FIELD OF THE INVENTION

The present invention relates to a blood purification apparatus comprising a blood purification instrument for extracorporeally circulating blood of a patient and a concentration detector for detecting a concentration of liquid flowing during blood purification.

BACKGROUND OF THE INVENTION

A hemodialysis treatment treats the blood of a patient by extracorporeally circulating the blood to purify it. In hemodialysis treatment, a dialyzer is used as a blood purification instrument for flowing therethrough a dialysate, and also connected to the dialyzer is a blood circuit for extracorporeally circulating blood of a patient through which the blood and the dialysate contact each other via dialysis membranes within the dialyzer so as to remove waste materials and excess water in blood (the removal of excess water is usually called as "ultrafiltration"). The blood purified by the dialyzer is returned into a body of the patient and, on the other hand, the blood waste material and excess water are discharged outside together with the dialysate via a dialysate discharging line.

The waste materials removed from blood contain urea, uric acid, creatinine etc. and it is found that a variation of the concentration of urea in blood is an effective indicator to show the dialysis efficiency. Accordingly, it has been proposed to monitor the variation in urea concentration to obtain proper dialysis efficiency. Although it is usually possible to know the variation in the urea concentration via a regularly performed blood examination, it is impossible to monitor the variation in urea concentration in real time during a dialysis treatment.

Accordingly, it has been proposed to arrange a discharged liquid concentration sensor on a dialysate discharging line so as to detect the variation in urea concentration (i.e. an indication such as "Kt/V") in real time (see e.g. JP 2002-516722 below). Such a conventional discharged liquid concentration sensor usually comprises LED(s) (light emitting means) for irradiating light on to discharged liquid from a dialyzer, a light receiving element(s) (light receiving means) for receiving light from the LED(s) transmitted through the discharged liquid, and a detecting means for detecting a received light intensity received by the light receiving element(s) and is structured so that the concentration of discharged liquid can be detected based on the received light intensity detected by the detecting means.

However in the blood purification apparatus of the prior art, there is concern that conditions for measuring discharged liquid concentration would be varied by every dialysis treatments due to reasons of individual difference or deterioration due to the aging of light emitting means of discharged liquid concentration sensors, differences in composition of dialysate flowing through a blood purification instrument or degree of fouling of measuring parts and thus the accuracy in detection of the discharged liquid concentration would be decreased. These problems may similarly occur in other concentration detecting means for detecting concentration of liquids (liquids flowing during blood purification treatment and including blood etc. other than dialysate) comprising a light emitting means and light receiving means, and thus improvement in accuracy has been desired.

It is, therefore, an object of the present invention to provide a blood purification apparatus that can improve the detecting accuracy of liquid concentration and, thus, the reliability of the concentration detecting means.

SUMMARY OF THE INVENTION

According to the present invention, there is provided a blood purification apparatus including a blood purification instrument for extracorporeally circulating blood of a patient and a concentration detecting means for detecting a concentration of liquid flowing during blood purification characterized in that the concentration detecting means comprises a light emitting means for irradiating light onto said liquid, a light receiving means for receiving light from the light emitting means transmitted through said liquid, a detecting means for detecting the received light intensity received by the light receiving means, and that the concentration detecting means can detect the concentration of the liquid based on the received light intensity detected by the detecting means and can be calibrated by adjusting an amount of irradiation by the light emitting means so that the received light intensity received by the light receiving means has a predetermined value.

It is preferable that the concentration detecting means comprises a light emission control means for controlling an amount of light emitted by the emitting means, a deciding means for deciding whether the received light intensity detected by the detecting means is substantially same as the predetermined value, and an adjusting means for making the light emission control means control the amount of light so that the received light intensity has the predetermined value based on the decision of the deciding means.

It is also preferable that the light emitting means includes LED(s) and the light receiving means has a light receiving element(s) generating a voltage corresponding to the received light intensity, and that the concentration detecting means is calibrated by adjusting a light emitting current of the light emitting means so that a voltage generated by the light receiving means has a predetermined value.

It is also preferable that the concentration detecting means is a discharged liquid concentration sensor which can monitor the blood purification efficiency by detecting the concentration of the liquid discharged from the blood purification instrument.

It is again preferable that the concentration detecting means is a blood leakage detector that can detect blood leakage from the concentration of discharged liquid from the blood purification instrument.

Further, the concentration detecting means is arranged on a blood circuit (which is arranged for extracorporeal circulation of blood of a patient) and has a blood concentration sensor that can detect the concentration of blood flowing through the blood circuit.

According to the present invention, since the concentration detecting means can detect the concentration of the liquid based on the received light intensity detected by the detecting means and can be calibrated by adjusting an amount of irradiation by the light emitting means so that the received light intensity received by the light receiving means has a predetermined value, it is possible to improve the detecting accuracy of liquid concentration and, thus, the reliability of the concentration detecting means.

According to an example, since the concentration detecting means comprises a light emission control means for controlling an amount of light emitted by the emitting means, a deciding means for deciding whether the received light intensity detected by the detecting means is substantially same as the predetermined value, and an adjusting means for making the light emission control means control the amount of light so that the received light intensity has the predetermined value based on the decision of the deciding means, it is possible to automatically perform the calibration of the concentration detecting means.

According to a further example, since the light emitting means comprises LED(s) and the light receiving means comprises a light receiving element(s) generating a voltage corresponding to the received light intensity, and the concentration detecting means is calibrated by adjusting a light emitting current of the light emitting means so that a voltage generated by the light receiving means has a predetermined value, it is possible to obtain a concentration detecting means having technical advantages of LED.

According to the present invention, since the concentration detecting means is a discharged liquid concentration sensor which can monitor the blood purification efficiency by detecting the concentration of the liquid discharged from the blood purification instrument, it is possible to improve the accuracy of detection of the concentration of discharged liquid during blood purification treatment and to monitor the efficiency of blood purification in real time with high accuracy.

According to the present example, since the concentration detecting means is a blood leakage detector which can detect blood leakage from the concentration of discharged liquid from the blood purification instrument, it is possible to improve the accuracy of blood leakage detection in discharged liquid during blood purification treatment.

Accordingly, since the concentration detecting means is arranged on a blood circuit, which is for extracorporeally circulate blood of a patient, and includes a blood concentration sensor which can detect the concentration of blood flowing through the blood circuit, it is possible to improve the accuracy in detection of blood concentration during the blood purification treatment.

DETAILED DESCRIPTION OF THE INVENTION

Examples of the present invention are described hereafter with reference to the drawings.

Figure 1:
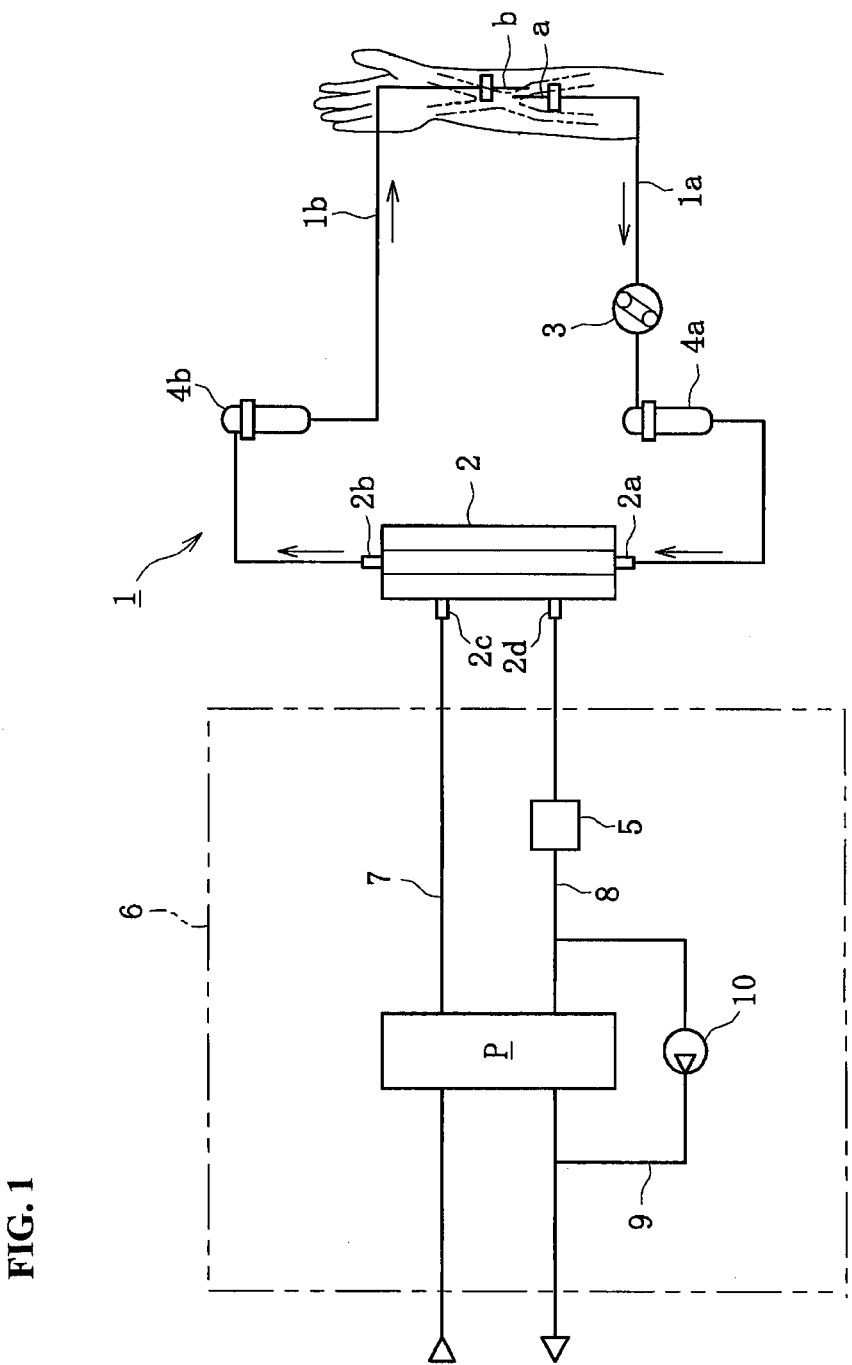
FIG. 1: A schematic view showing an embodiment of the blood purification apparatus of the present invention.

A blood purification apparatus is used for purifying blood of a patient with its extracorporeal circulation and can be applied to a hemodialysis apparatus used in hemodialysis treatment. As shown in FIG. 1, such a hemodialysis apparatus generally comprises a dialyzer 2 as a blood purification instrument, a blood circuit 1 connected to the dialyzer 2, a discharged liquid concentration sensor 5 as a concentration detecting means, and a dialysis apparatus body 6 for performing ultrafiltration while supplying dialysate to the dialyzer 2.

The blood circuit 1 mainly includes as shown in FIG. 1 an arterial blood circuit 1a and a venous blood circuit 1b respectively formed of a flexible tube and the dialyzer 2 is arranged between these blood circuits 1a, 1b and connected to them. An arterial puncture needle "a" is adapted to be connected to a tip of the arterial blood circuit 1a, and a peristaltic blood pump 3 and a drip chamber 4a for bubble removal are arranged on the arterial blood circuit 1a. On the other hand, a venous puncture needle "b" is adapted to be connected to a tip of the venous blood circuit 1b, and a drip chamber 4b for bubble removal is arranged on the venous blood circuit 1b.

Once the arterial puncture needle "a" and the venous puncture needle "b" are respectively punctured into an artery and a vein of a patient, and the blood pump 3 is started, the blood of a patient flows through the arterial blood circuit 1a to the dialyzer 2 via the drip chamber 4a for bubble removal. The blood of a patient is purified and ultrafiltrated and finally returned to the vein of a patient through the venous blood circuit 1b after having air bubbles removed by the drip chamber 4b. That is, the blood of a patient can be purified by the dialyzer 2 via the extracorporeal circulation through the blood circuit 1.

A casing of the dialyzer 2 is provided with a blood inlet port 2a, a blood outlet port 2b, a dialysate inlet port 2c and a dialysate outlet port 2d. A base end of the arterial blood circuit 1a is connected to the blood inlet port 2a and a base end of the venous blood circuit 1b is connected to the blood outlet port 2b. In addition, a dialysate introducing line 7 and a dialysate discharging line 8, both formed by extending dialysis apparatus body 6, are connected respectively to the dialysate inlet port 2c and the dialysate outlet port 2d.

A large number of hollow fibers (not shown) are contained within the dialyzer 2 and a hollow space of each fiber forms a flowing passage of blood and a space formed by an outer circumferential surface of each fiber and an inner circumferential surface of the casing of the dialyzer 2 forms a flowing passage of dialysate. A wall of each hollow fiber is formed with a vast number of micro apertures (pores) passing through the wall between its inner and outer circumferential surfaces and thus the wall forms a membrane of the hollow fiber. Thus the waste materials and excess water etc. in blood can pass through the membrane of the hollow fiber into the dialysate flowing around each hollow fiber.

On the other hand, the dialysis apparatus body 6 includes mainly a duplex pump P, a bypass line 9 connected to the dialysate discharging line 8 bypassing the duplex pump P, and an ultrafiltration pump 10 arranged on the bypass line 9. The duplex pump P is arranged as bridging the dialysate introducing line 7 and the dialysate discharging line 8 and used for supplying the dialysate to the dialyzer 2 through the dialysate introducing line 7 and discharging the dialysate from the dialyzer 2 together with waste material in blood through the dialysate discharging line 8.

One end of the dialysate introducing line 7 is connected to the dialysate inlet port 2c of the dialyzer 2 and the other end of the dialysate introducing line 7 is connected to a dialysate supplying apparatus (not shown), which is for preparing dialysate of predetermined concentration. In addition, one end of the dialysate discharging line 8 is connected to the dialysate outlet port 2d of the dialyzer 2 and the other end of the dialysate discharging line 8 is connected to a solution discharging means (not shown). Accordingly, the dialysate supplied from the dialysate supplying apparatus to the dialyzer 2 through the dialysate introducing line 7 is adapted to be returned from the dialyzer 2 to the solution discharging means through the dialysate discharging line 8 and the bypass line 9.

The ultrafiltration pump 10 is used for removing water from blood of a patient flowing in the dialyzer 2. In particular, an amount of a liquid discharged from the dialysate discharging line 8 becomes more than an amount of the dialysate introduced to the dialyzer 2 through the dialysate introducing line 7 when the ultrafiltration pump 10 is driven and the increased amount of the liquid corresponds to an amount of water removed from blood. It may be possible to remove water from blood of a patient by using means (e.g. a so-called "balancing chamber" etc.) other than the ultrafiltration pump 10.

Figure 3:
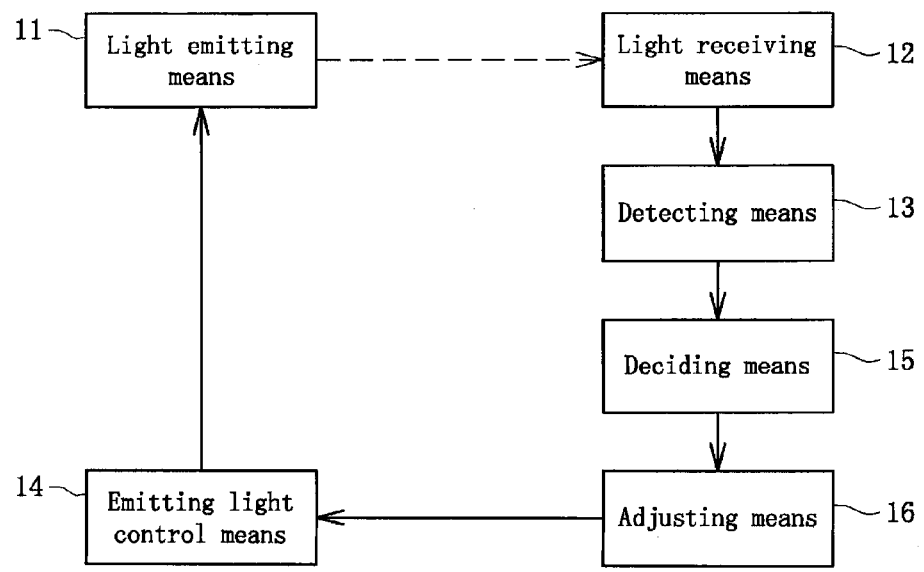
FIG. 3: A block diagram showing the concentration detecting means of FIG. 2.

The discharged liquid concentration sensor (concentration detecting means) 5 is arranged on the dialysate discharging line 8 within the dialysis apparatus body 6 to monitor the efficiency of blood purification by detecting concentration of a liquid (liquid discharged from the dialyzer 2 as a blood purification instrument in the present invention) flowing during the blood purification treatment and mainly includes, as shown in FIG. 3, a light emitting means 11, a light receiving means 12, a detecting means 13, an emitting light control means 14, a deciding means 15, and an adjusting means 16.

Figure 2:
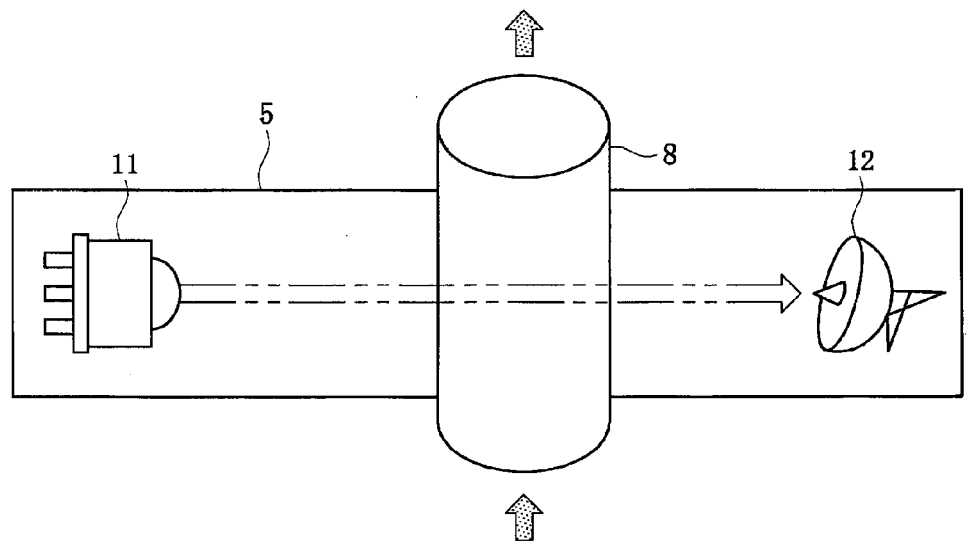
FIG. 2: An enlarged schematic view showing a concentration detecting means of the blood purification apparatus of FIG. 1.

The light emitting means 11 is a light source comprising LED(s) irradiating light onto the liquid (liquid discharged from the dialyzer 2 in the present invention) and arranged oppositely to the light receiving means 12 via the dialysate discharging line 8 as shown in FIG. 2. The light receiving means 12 is intended to receive light from the light emitting means 11 transmitted through the liquid (liquid discharged from the dialyzer 2) and includes light receiving element(s) generating a voltage corresponding to a received light intensity.

When light from the light emitting means 11 is irradiated onto the dialysate discharging line 8 through which discharged liquid flows, the irradiated light is transmitted through the discharged liquid after being absorbed by an amount corresponding to the concentration of the discharged liquid and received by the light receiving means 12. Thus, it is possible to detect the variation of concentration of the discharged liquid by detecting the received light intensity (i.e. a voltage generated in accordance with the received light intensity) using the light receiving means 12.

The detecting means 13 is electrically connected to the light receiving means 12 to detect the received light intensity (voltage in accordance with the received light intensity in the present invention) of the light receiving means 12. The emitting light control means 14 is intended to control an amount of emitting light by the light emitting means 11 and has e.g. a digital amplifier that can control a current supplied to the light emitting means 11.

The deciding means 15 is electrically connected to the detecting means 13 and adapted to decide whether the received light intensity (voltage caused corresponding to the received light intensity of the light receiving means 12) detected by the detecting means 13 is substantially same as the predetermined value. The adjusting means 16 is electrically connected to both the deciding means 15 and the emitting light control means 14 and adapted to make the emitting light control means 14 control the amount of emitting light so that the received light intensity (voltage caused corresponding to the received light intensity of the light receiving means 12) has a predetermined value based on a decision of the deciding means 15.

It is possible according to the structure of the present invention to detect the concentration of discharged liquid flowing through the dialysate discharging line 8 based on the received light intensity (voltage caused corresponding to the received light intensity of the light receiving means 12) detected by the detecting means 13. In addition according to an example the discharged liquid concentration sensor (concentration detecting means) 5 can be calibrated by adjusting the amount of irradiating light by the light emitting means 11 so that the received light intensity (voltage caused corresponding to the received light intensity of the light receiving means 12) of the light receiving means 12 has a predetermined value.

Figure 4:
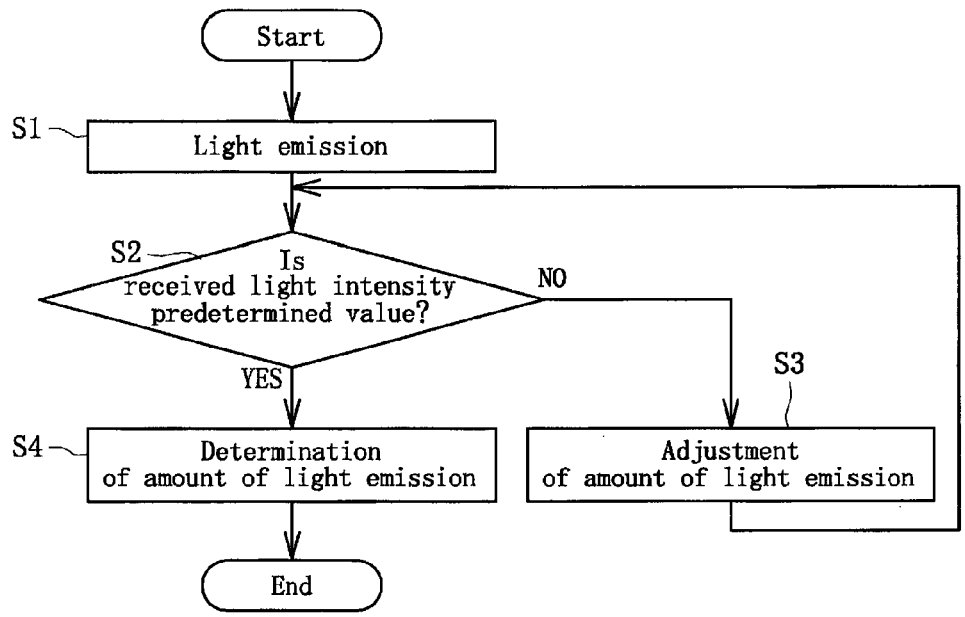
FIG. 4: A flowchart showing a control of the concentration detecting means of FIG. 2.

Next, a method for calibrating the discharged liquid concentration sensor (concentration detecting means) 5 is described with reference to a flowchart of FIG. 4.

Prior to the blood purification treatment (i.e. prior to the dialysis treatment as well as prior to the extracorporeal circulation of blood through the blood circuit 1), the dialysate is supplied to the dialyzer 2 by driving the duplex pump P and the dialysate is discharged from the dialyzer 2 through the dialysate discharging line 8. Under such a condition a light is emitted by the light emitting means 11 (S 1) and a decision is performed by the deciding means 15 whether a received light intensity (voltage caused corresponding to the received light intensity of the light receiving means 12) detected by the detecting means 13 is substantially same as the predetermined value (S 2).

Adjustment of the amount of light emission of the light emitting means 11 is performed by the emitting light control means 14 (S 3) when it is decided in the step S 2 that the received light intensity (voltage caused corresponding to the received light intensity of the light receiving means 12) detected by the detecting means 13 is not substantially same as the predetermined value. In this time when it is decided that the received light intensity is less than the predetermined value, the emitting light control means 14 controls to increase the amount of light emission of the light emitting means 11 and this operation is repeated until the received light intensity becomes substantially same as the predetermined value. On the contrary, when it is decided that the received light intensity is larger than the predetermined value, the emitting light control means 14 controls to decrease the amount of light emission of the light emitting means 11 and this operation is repeated until the received light intensity becomes substantially same as the predetermined value.

When it is decided at the step S 2 that the received light intensity (voltage caused corresponding to the received light intensity of the light receiving means 12) detected by the detecting means 13 is substantially same as the predetermined value, the amount of light emission of the light emitting means 11 is determined and the light emitting means 11 emits a light at the determined amount of light emission (S 4).

Thus, the calibration of the discharged liquid concentration sensor (concentration detecting means) 5 has been completed.

It is possible to detect the concentration (variation of concentration) of discharged liquid flowing through the dialysate discharging line 8 based on the received light intensity (voltage caused corresponding to the received light intensity of the light receiving means 12) detected by the detecting means 13 when performing the dialysis treatment with extracorporeally circulating blood of a patient through the blood circuit 1 after the calibration described above. Thus it is also possible to monitor the efficiency of blood purification in real time during a dialysis treatment by operating e.g. an indication such as "Kt/V" based on the concentration variation.

"Kt/V" is an indicator obtained by substituting the urea nitrogen concentration at times of both commencement and completion of the hemodialysis treatment, a total amount of ultrafiltration during the hemodialysis treatment and a time duration of the ultrafiltration in a predetermined mathematical expression e.g. such as Kt/V=−1 n(Ce/Cs) (herein "Ce" is the urea nitrogen concentration at time of completion of the hemodialysis treatment and "Cs" is the urea nitrogen concentration at time of commencement of the hemodialysis treatment). In general, it is possible from this indication to judge that the dialysis efficiency is proper if the value of Kt/V is 1.2 or more. According to the present invention, since the variation of urea nitrogen concentration can be known in real time from the operational expression above, it is possible to monitor the blood purification efficiency in real time during the blood purification treatment (hemodialysis treatment).

According to the present invention, since the concentration of liquid can be detected based on the received light intensity detected by the detecting means 13 and the discharged liquid concentration sensor (concentration detecting means) 5 can be calibrated by adjusting the amount of light irradiation of the light emitting means 11 so that the received light intensity of the light receiving means 12 becomes the predetermined value, it is possible to improve the accuracy of concentration detection of liquid (discharged liquid) by the discharged liquid concentration censor 5 and thus the reliability of the discharged liquid concentration censor (concentration detecting means) 5.

Figure 5:
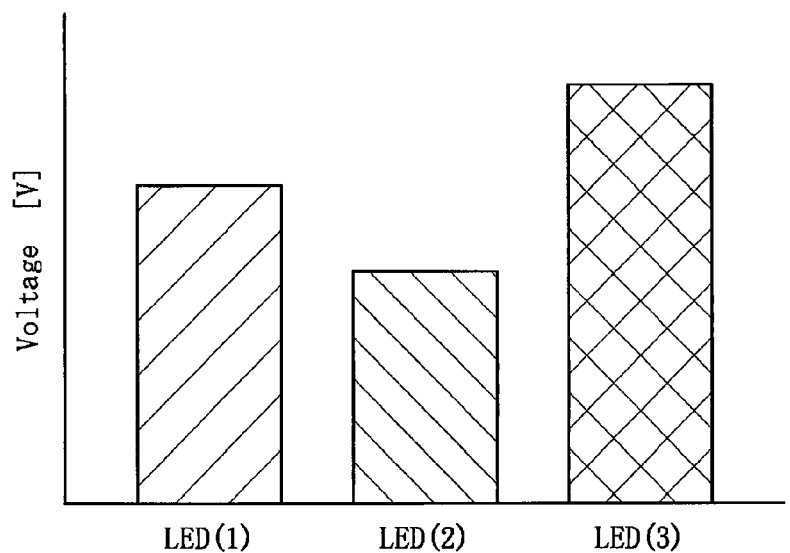
FIG. 5: A graph showing a variation of received light voltage due to individual difference of the light emitting means of the concentration detecting means.
Figure 6:
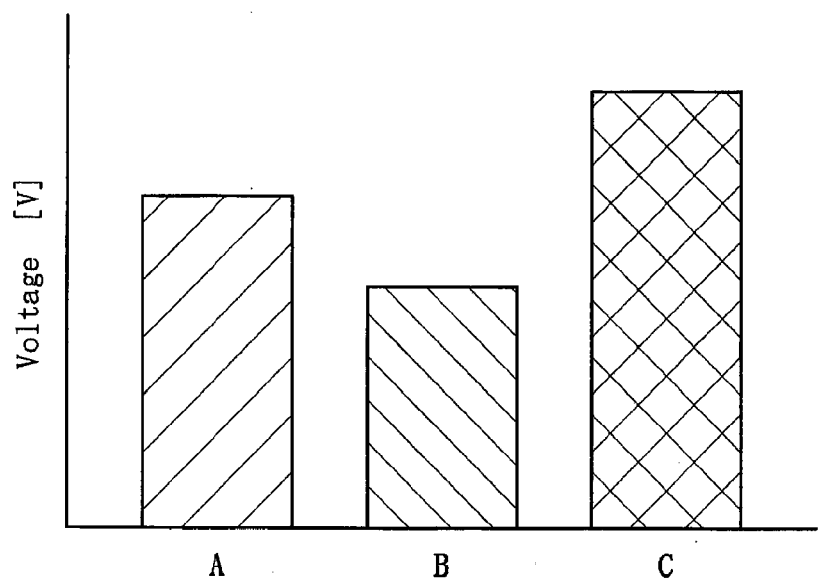
FIG. 6: A graph showing a variation of received light voltage due to difference of dialysate in the concentration detecting means.
Figure 7:
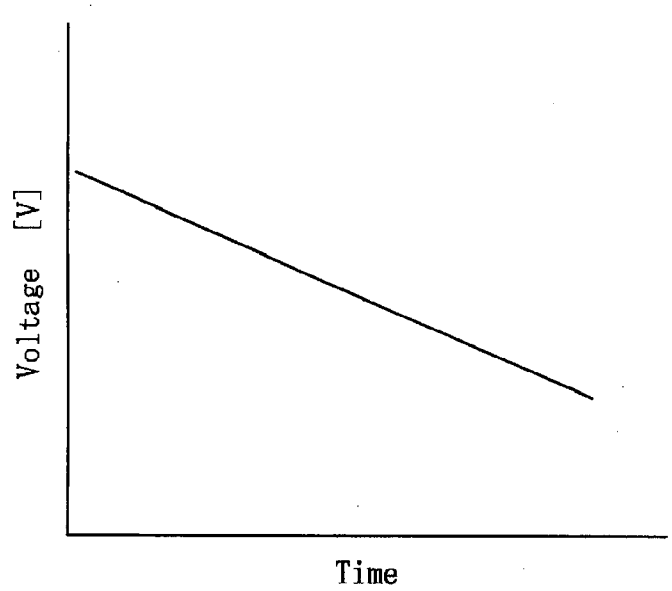
FIG. 7: A graph showing a variation of received light voltage due to deterioration caused by aging of the light emitting means of the concentration detecting means.

In the blood purification apparatus of the prior art, conditions of concentration detection during the blood purification treatment are liable to be changed because of: individual differences of LEDs which cause differences in light emitting intensity in the light emitting means 11 although same amount of electric current is supplied to them (see LEDs (1)-(3) in FIG. 5); differences in composition of dialysates flowing through the dialyzer (blood purification instrument) 2 which cause differences in the received light intensity (voltage caused by received light) of the light receiving means 12 although the irradiation is carried out by the light emitting means 11 under a same emitting light intensity (see FIG. 6); and deterioration of the emitting light intensity of a same light emitting means 11 with passage of time (see FIG. 7). On the contrary, according to the example, since the discharged liquid concentration sensor (concentration detecting means) 5 can be calibrated by adjusting the amount of irradiation by the light emitting means 11 so that the received light intensity of the light receiving means 12 has a predetermined value, it is possible to improve the accuracy of concentration detection of discharged liquid by the discharged liquid concentration censor 5 by absorbing differences in conditions of concentration detection such as individual differences of LEDs and thus the reliability of the discharged liquid concentration censor (concentration detecting means) 5. Furthermore, according to the present invention it is possible to absorb difference in conditions such as soil of the light emitting means 11, light receiving means 12 and dialysate discharging line (flow passage of liquid) 8.

Figure 8:
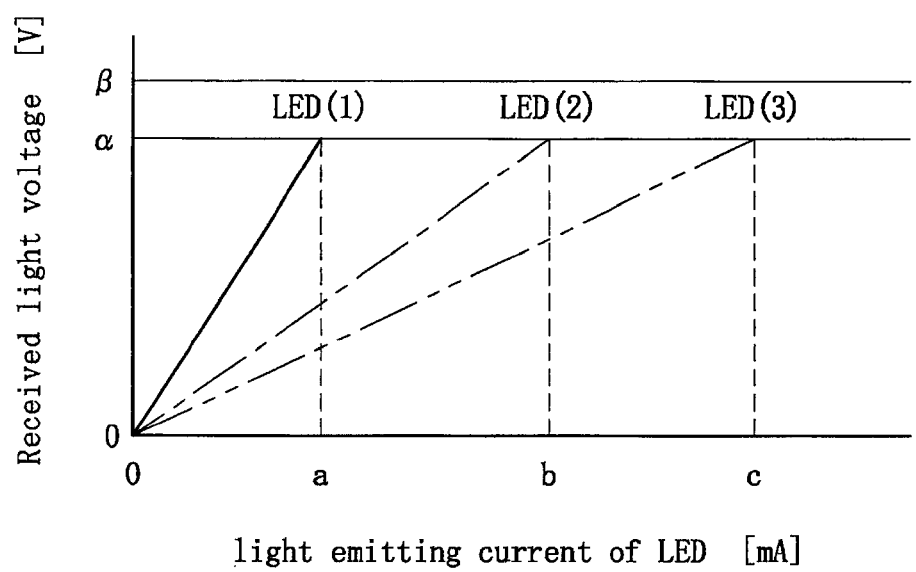
FIG. 8: A graph showing an adjustment for absorbing the individual difference of the light emitting means in the concentration detecting means.

According to the present invention, since the discharged liquid concentration censor (concentration detecting means) 5 is calibrated by adjusting the amount of emitting light by the light emitting means 11 so that the received light intensity of the light receiving means 12 has a predetermined value, a current of "a" (mA) for the LED (1) applied as the light emitting means 11, a current of "b" (mA) for the LED (2) and a current of "c" (mA) for the LED (3) are supplied to them when the predetermined value (received light voltage) is α (V) as shown in FIG. 8. Herein if the predetermined value of the received light intensity by the received light means 12 is defined as a voltage β, it is preferable to set both "α" and "β" in a range 4.5-5.0 (V).

Further, according to the present invention since the discharged liquid concentration censor (concentration detecting means) 5 includes the emitting light control means 14 that is able to control the amount of emitting light by the light emitting means 11, the deciding means 15 that decides whether the received light intensity detected by the detecting means 13 is substantially same as the predetermined value, and the adjusting means 16 that makes the emitting light control means 14 control the amount of emitting light so that the received light intensity has the predetermined value, it is possible to perform the calibration of the discharged liquid concentration censor (concentration detecting means) 5 automatically.

In addition, since the light emitting means 11 has LED(s) and the light receiving means 12 includes light receiving element(s) being able to generating a voltage corresponding to the received light intensity, and the discharged liquid concentration censor (concentration detecting means) 5 can be calibrated by adjusting the light emitting current of the light emitting means 11 so that the voltage caused by the light receiving means 12 has the predetermined value, it is possible to obtain the discharged liquid concentration censor (concentration detecting means) 5 having technical advantages (e.g. features of long life and resistance against heat for a long term light emission) of LED(s).

In addition, according to the present invention since the concentration detecting means comprises the discharged liquid concentration sensor 5 which can monitor the blood purification efficiency by detecting the concentration of discharged liquid from the dialyzer (blood purification instrument) 2, it is possible to improve the accuracy of detection of concentration of discharged liquid during the blood purification treatment and to monitor the blood purification efficiency in real time with high accuracy. Although it is described in the present invention that the blood purification efficiency (dialysis efficiency) is obtained by calculating the indication of Kt/V from the concentration of discharged liquid detected by the discharged liquid concentration sensor 5, it is also possible to obtain the blood purification efficiency (dialysis efficiency) by calculating other indications.

The concentration detecting means is not limited to the discharged liquid concentration sensor 5 and may be formed of a blood leakage detector which is arranged on the dialysate discharging line 8 within the dialysis apparatus 6 and is able to detect leaked blood from a concentration of liquid discharged from the dialyzer (blood purification instrument) 2, or may be formed of a blood concentration detecting sensor (e.g. a hematocrit sensor for measuring the hematocrit value of blood) which is arranged on the blood circuit 1 for extracorporeally circulating blood of a patient and is able to detect the concentration of blood flowing through the blood circuit 1.

If the concentration detecting means is a blood leakage detector which is able to detect leaked blood from a concentration of liquid discharged from the dialyzer (blood purification instrument) 2, it is possible to improve the accuracy of detection of blood leakage in discharged liquid during blood purifying treatment. On the other hand, if the concentration detecting means is a blood concentration detecting sensor which is arranged on the blood circuit 1 for extracorporeally circulating blood of a patient and is able to detect the concentration of blood flowing through the blood circuit 1, it is possible to improve the accuracy of detection of blood concentration during blood purifying treatment.

The present invention has been described with reference to the above example. Obviously, modifications and alternations will occur to those of ordinary skill in the art upon reading and understanding the preceding detailed description. For example, it is possible to apply the present invention to concentration detecting sensor being able to detect the concentration of liquid in the blood purification apparatus other than the discharged liquid concentration sensor, blood leakage detector or blood concentration sensor etc. In addition, the emitting light control means 14 may be a manually operable one not having the decision means 15 and the adjusting means 16, if it is able to detect the concentration of liquid based on the received light intensity detected by the detecting means 13 and also is able to calibrate the concentration detecting means by adjusting the amount of light irradiation by the light emitting means 11 so that the received light intensity of the light receiving means 12 has the predetermined value. That is, it is possible to manually adjust an amount of irradiating light irradiated by the light emitting means 11 so that the received light intensity of the light receiving means 12 has the predetermined value.

Furthermore, although it is described in the example that LED(s) is used as the light emitting means, other appropriate means (e.g. UV lamp, halogen lamp, fluorescent lamp, organic electroluminescent device) may be used as a light source. Although it is described that the present invention is applied to a hemodialysis apparatus, it is possible to apply the present invention to a blood purification apparatus used in other treatments (e.g. blood filtration treatment or blood filtrating dialysis treatment etc.) performing blood purification by an extracorporeal circulation.

The present invention can be applied to a blood purification apparatus having additional functions if the blood purification apparatus is that which can detect concentration of liquid based on a received light intensity detected by a detecting means and calibrate the concentration detecting means by adjusting the amount of light irradiation by the light emitting means so that the received light intensity of the light receiving means has the predetermined value.

What is claimed is:

1. A blood purification apparatus comprising:
a blood purification instrument for extracorporeally circulating blood of a patient; and
a concentration detector for detecting a concentration of liquid flowing during blood purification, the liquid including a dialysate and the blood of the patient, the concentration detector comprising:
a light emitter configured to irradiate the liquid with light,
a light receiver configured to receive the light from the light emitter transmitted through the liquid, and
a detector configured to detect intensity of the light received by the light receiver, the concentration of the liquid being determined based on the intensity of the received light, and
a controller programmed to perform calibration of the concentration detector before the blood purification instruction starts circulating the blood of the patient, in which the controller is programmed to supply only the dialysate to the concentration detector to adjust an amount of light emission from the light emitter so that the intensity of the received light has a predetermined value, wherein
when the controller determines that the intensity of the received light is greater than a predetermined value, the controller controls the light emitter to reduce the amount of the light emission, and
when the controller determines that the intensity of the received light is smaller than the predetermined value, the controller controls the light emitter to increase the amount of the light emission.

2. The blood purification apparatus of claim 1 wherein the controller further configured to:
determine whether the received light intensity detected by the detector is substantially same as the predetermined value, and
based on the determination, control the light emitter so that the received light intensity has the predetermined value.

3. The blood purification apparatus of claim 1 wherein
the light emitter comprises LED(s), and
the light receiver comprises a light receiving element(s) generating a voltage corresponding to the received light intensity, wherein
the controller adjusts light emitting current of the light emitter so that a voltage generated by the light receiver has a predetermined value.

4. A blood purification apparatus comprising:
a blood purification instrument for extracorporeally circulating blood of a patient; and
a concentration detector for detecting a concentration of liquid flowing during blood purification, the liquid including a dialysate and the blood of the patient, the concentration detector comprising:
a light emitter configured to irradiate the liquid with light,
a light receiver configured to receive the light from the light emitter transmitted through the liquid, and
a detector configured to detect intensity of the light received by the light receiver, the concentration of the liquid being determined based on the intensity of the received light, and
a controller programmed to perform calibration of the concentration detector before the blood purification instruction starts circulating the blood of the patient, in which the controller is programmed to supply only the dialysate to the concentration detector to adjust an amount of light emission from the light emitter so that the intensity of the received light has a predetermined value, wherein
when the controller determines that the intensity of the received light is greater than a predetermined value, the controller controls the light emitter to reduce the amount of the light emission,
when the controller determines that the intensity of the received light is smaller than the predetermined value, the controller controls the light emitter to increase the amount of the light emission, and
the concentration detector is a discharged liquid concentration sensor configured to monitor the blood purification efficiency by detecting the concentration of the liquid discharged from the blood purification instrument.

5. The blood purification apparatus of claim 1 wherein the concentration detector is a blood leakage detector configured to detect blood leakage from the concentration of discharged liquid from the blood purification instrument.

6. The blood purification apparatus of claim 1 wherein the concentration detector is arranged on a blood circuit and comprises a blood concentration sensor configured to detect the concentration of blood flowing through the blood circuit.

* * * * *